United States Patent [19]

Roberts

[11] Patent Number: 4,958,635
[45] Date of Patent: Sep. 25, 1990

[54] THERAPEUTIC TEMPERATURE PACK
[75] Inventor: Frank L. Roberts, Willowdale, Canada
[73] Assignee: Bio-Support Industries Ltd., Toronto, Canada
[21] Appl. No.: 326,839
[22] Filed: Mar. 21, 1989
[51] Int. Cl.⁵ .............................................. A61F 7/02
[52] U.S. Cl. ...................................... 128/403; 62/530
[58] Field of Search ............... 128/403, 402, 379, 380, 128/82.1; 62/530, 259.3; 383/901

[56] References Cited

U.S. PATENT DOCUMENTS

| 2,043,327 | 6/1936 | Miller | 128/403 |
| 2,602,302 | 7/1952 | Poux | 62/530 |
| 3,092,112 | 6/1963 | Zelony | 128/403 |
| 4,404,820 | 9/1983 | Romaine | 62/530 |
| 4,575,097 | 3/1986 | Brannigan et al. | 62/530 |
| 4,596,250 | 6/1986 | Beisang, III et al. | 128/403 |

Primary Examiner—Edward M. Coven
Assistant Examiner—Mark S. Graham
Attorney, Agent, or Firm—Kenneth M. Garrett

[57] ABSTRACT

A temperature pack for therapeutic use comprises a sealed envelope of flexible sheet plastic material and a thickened aqueous composition contained within the envelope. At least one major surface of the envelope is embossed with a plurality of small blisters, which substantially increases the ability of the bag to conform to body contours. The sheet plastic material is preferably metallized to reduce undesired heat transfer.

12 Claims, 1 Drawing Sheet

THERAPEUTIC TEMPERATURE PACK

FIELD OF THE INVENTION

This invention relates to therapeutic temperature packs which find use in external application to the body to elevate or lower the temperature in localized areas for therapeutic purposes.

BACKGROUND OF INVENTION

Generally, such packs comprise a thin, planar plastic film formed in an envelope containing therein a liquid medium which is either cooled or warmed prior to application to the body. One of the disadvantages of such packs is that they do not readily conform to body contours, particularly around joint areas. The shaping forces tend to collapse the bags over a relatively wide area, so reducing the amount of liquid medium in those areas where it is most needed.

The liquid medium contained in reusable therapeutic packs, particularly where they are for use in cooling is normally water, together with a freezing point depressant such as propylene glycol or glycerol, whereby the liquid medium will be frozen to a slush of ice crystals at normal freezer temperatures, about 0° F. Because of the low conformability of the planar film bags, relatively high concentrations of freezing point depressant are employed, so as to form only a thin slush of ice crystals. This increases the manufacturing cost of the packs, but more importantly, it reduces the heat capacity very significantly in comparison to a crushed ice pack, and it does not permit adequate treatment times with a single therapeutic pack of normal dimensions.

SUMMARY OF THE INVENTION

In accordance with this invention, a therapeutic pack of the foregoing nature has an envelope formed from a planar, plastic film having a plurality of small blisters raised on at least medial surface portions of the envelope on at least one major surface thereof. Suitably such blisters will individually have a plan form surface area of not more than about 200 mm$^2$ and preferably about 100 mm$^2$. Collectively they will occupy from about one half to three quarters of the planar surface area of the portion of the film on which they are raised, the other one half to one quarter of the surface forming a two dimensional chain-like web interconnecting the blisters. Such blisters permit a localized deformation and crushing of the envelope without it collapsing over a wide area, and the envelope more readily conforms to body contours. Accordingly, the rate of heat transfer to or from the pack is appreciably more uniform over longer periods of time in comparison to the prior art devices.

Although the blisters may be formed over both major surfaces of the envelope, it is preferred that they be formed on one major surface only. This is found not to limit the conformability of the pack unduly, in comparison to where the blisters are formed on both major surfaces, and it reduces undesired heat transference across surfaces of the pack that are not adjacent to the body member being treated.

Due to the ease of conformation of the envelope, whether the blisters are formed on one or both major surfaces, it is found that thick ice slushes may be used, thereby increasing the heat capacity of cooling packs significantly, and accordingly treatment times may be increased to therapeutically desirable durations.

In accordance with a further aspect of the invention, the plastic film of the envelope may be coated with a heat reflective layer, suitably by vacuum metallization, to reduce the rate of heat transfer. Desirably the metallic layer will be laminated between film layers so as to resist attack by the liquid medium and surface abrasion.

These foregoing objects and aspects of the invention, together with other objects, aspects and advantages thereof will be more apparent from the following description of a preferred embodiment thereof, taken in conjunction with the following drawings.

DESCRIPTION OF THE PREFERRED EMBODIMENT

Figure 1:
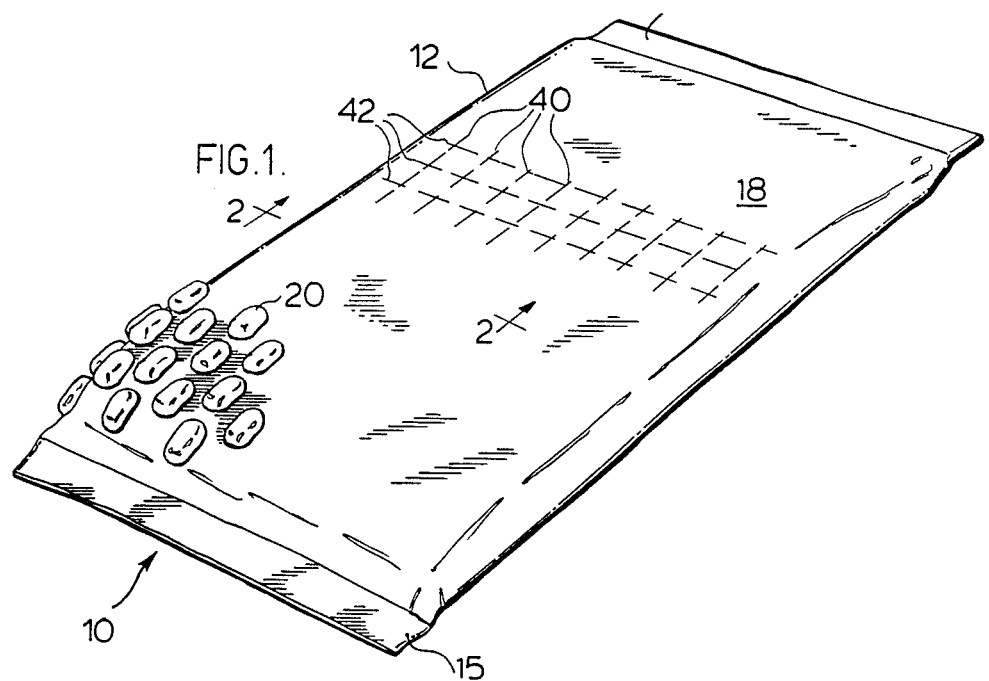
FIG. 1—is a plan view of a therapeutic temperature pack constructed in accordance with the invention showing a small portion only of the surface embossed with blisters for ease of illustration.
Figure 2:
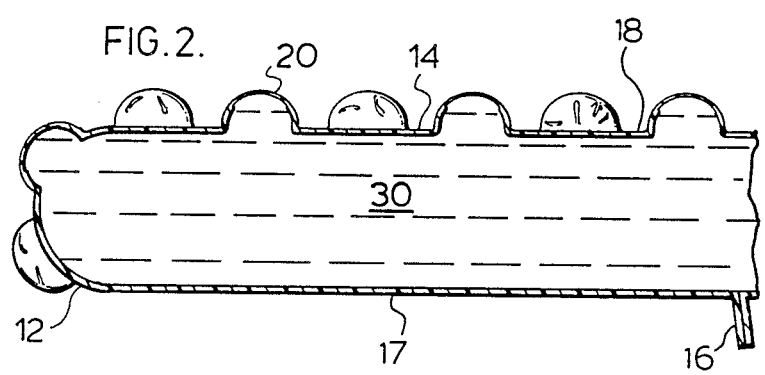
FIG. 2—is a cross secton along transverse plane 2—2 of FIG. 1.
Figure 3:
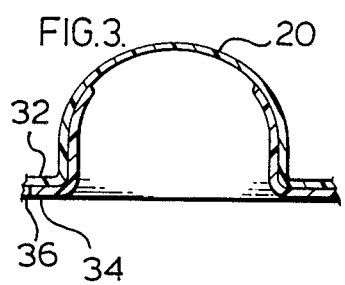
FIG. 3—is an axial cross section through one blister on enlarged scale.

Considering the drawings in detail, a therapeutic temperature pack in accordance with the invention is identified generally therein by the numeral 10. Pack 10 comprises an envelope-like bag 12 which is conveniently formed from a single sheet of plastic material 14 by fusion welding, or otherwise joining in any convenient, impervious, manner the sides and ends respectively at seams 15,16. Bag 12 has opposed major surfaces 17,18. Prior to the seaming operation, the sheet is embossed to raise small, outward blisters 20 over the whole of one of the major surfaces thereof, here surface 18. It will be appreciated that those areas to be seamed will not be embossed. Individual blisters 20 have a planform surface area of about 100 mm$^2$, and a volume of about 300 mm$^3$. Cumulatively, blisters 20 occupy about 65% of the major surface area of bag 12 on which they locate, and a volume of some 1 to 3% of the total volume of the bag 12 when filled with a liquid medium 30.

Plastic sheet material 14 is a composite structure comprising opposed sheets 32,34 one of which is coated with a thin layer of aluminum 36 by known metallizing technique, which sheets are then laminated together to sandwich the thin metallized layer 36 therebetween. Suitably, sheet material 14 will have a thickness of about 0.15 mm (006 inch). Normally the wall of blisters 20 in central portions thereof will have a thickness of about one third that of the sheet thickness. The aluminum film 36 will suitably be very thin, a few microns only. Materials of this nature are currently available in commerce.

Figure 4:
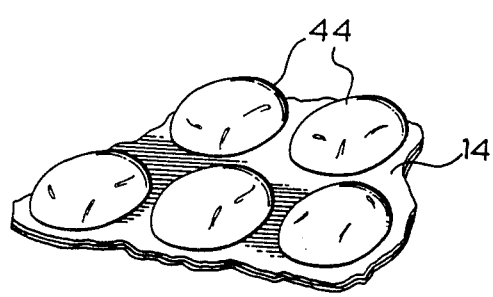
FIG. 4—shows in perspective view a small surface portion of a second embodiment of a temperature pack, with a somewhat differently shaped blister than in the first embodiment.

Generally speaking pack 10 will have blisters 20 disposed on the surface thereof in a uniform grid arrangement of lengthwise columns 40 and transverse rows 42. In order to maximize the conformability of pack 10 in the lengthwise direction, adjacent blisters 20 in each column will be axially aligned, whereas blisters 20 of alternate rows only are transversely aligned. Preferably, at least where pad 10 is intended primarily for use as an ice pack, blisters 20 are elongated somewhat in the columnar direction, to have a generally oval planform.

Where pack 10 is intended primarily for use at elevated temperatures, it is preferred that the blisters have a circular plan form and are generally spherical caps, as identified in FIG. 4 by the numeral 44.

Liquid medium 30 contained within layer 12 suitably comprises about 80 parts of water to 25 parts of propylene glycol, and forms a thick slush of ice crystals at 0° F. which readily yields under hand pressure to become pliable, whereby the pack 10 may be easily conformed to body contours. Other conventional additives such as thickeners, stabilizers and colourants may also be included in the composition as will be known to persons in the art.

It will be apparent that many changes may be made to the illustrative embodiment, while falling within the scope of the invention and it is intended that all such changes be covered by the claims appended hereto.

I claim:

1. In a temperature pack for therapeutic use comprising a sealed envelope-like bag of flexible sheet plastic material, said bag having an interior, and a thickened aqueous liquid composition contained within said interior of said bag, the improvement wherein said plastic sheet material is embossed to form a large plurality of small blisters on at least medial portions of at least one major surface of said bag, said blisters
   (i) being open to the interior of said bag
   (ii) cumulatively having a volume of not greater than about 3% of the total volume of said liquid composition contained within said bag.

2. A temperature pack as defined in claim 1, wherein said blisters occupy from about one half to two thirds of the portion of the embossed surface area of said bag.

3. A temperature pack as defined in claim 1, wherein said sheet material is embossed to form said blisters over one major surface only of said bag.

4. A temperature pack as defined in claim 1, wherein said blisters have a wall thickness less than the thickness of said sheet plastic material.

5. A temperature pack as defined in claim 1, wherein said blisters are arranged symmetrically in columns and rows, and adjacent blisters in any column are in alignment.

6. A temperature pack as defined in claim 5, wherein alternate rows of blisters are in alignment.

7. A temperature pack as defined in claim 1, wherein said bag has a length greater than the width thereof, and wherein said blisters have a plan form elongated along the length of the bag.

8. A temperature pack as defined in claim 5, wherein said blisters are in the form of spherical caps.

9. A temperature pack as defined in claim 1, wherein said plastic material is coated with a metallic film.

10. A temperature as defined in claim 9, wherein said metallic film is sandwiched in said plastic material.

11. A temperature pack as defined in claim 7, wherein said aqueous composition comprises water and propylene glycol in a weight ratio of not less than about 7:3.

12. A temperature pack as defined in claim 7, wherein said aqueous composition includes a thickner and stabilizer therefor.

* * * * *